(12) United States Patent
Coifman

(10) Patent No.: US 9,107,901 B2
(45) Date of Patent: Aug. 18, 2015

(54) IMMUNOTHERAPY COMPOSITIONS AND METHODS OF TREATMENT

(76) Inventor: Robert E. Coifman, Milville, NJ (US)

( * ) Notice: Subject to any disclaimer, the term of this patent is extended or adjusted under 35 U.S.C. 154(b) by 131 days.

(21) Appl. No.: 13/008,945

(22) Filed: Jan. 19, 2011

(65) Prior Publication Data

US 2011/0177128 A1 Jul. 21, 2011

Related U.S. Application Data

(60) Provisional application No. 61/336,205, filed on Jan. 19, 2010, provisional application No. 61/336,799, filed on Jan. 27, 2010, provisional application No. 61/398,170, filed on Jun. 22, 2010.

(51) Int. Cl.

| | | |
|---|---|---|
| *A61K 31/00* | (2006.01) |
| *A61K 39/00* | (2006.01) |
| *A61K 39/35* | (2006.01) |
| *A61K 39/36* | (2006.01) |
| *A61K 39/38* | (2006.01) |

(52) U.S. Cl.
CPC .............. *A61K 39/35* (2013.01); *A61K 2039/54* (2013.01); *A61K 2039/55505* (2013.01)

(58) Field of Classification Search
None
See application file for complete search history.

(56) References Cited

U.S. PATENT DOCUMENTS

| 4,259,318 | A | * | 3/1981 | Duhe et al. .................... 424/94.4 |
| 5,767,109 | A | * | 6/1998 | Sanchez et al. ................ 514/58 |
| 2003/0152641 | A1 | | 8/2003 | Iyer et al. |
| 2008/0063667 | A1 | | 3/2008 | Jacquet et al. |

OTHER PUBLICATIONS

Kalish et al. 'Urushiol (Poison Ivy)-triggered Suppressor T Cell Clone Generated from Peripheral Blood.' J. Clin. Invest. 82:825-832, 1988.*
ElSohly et al. 'Separation and Characterization of Poison Ivy and Poison Oak Urushiol Components.' J. Nat. Prod. 45 (5):532-538, 1982.*
Symes et al. 'Poison Ivy Urushiol.' J. Am. Chem. Soc. 76 (11):2959-2963, 1954.*
Epstein et al. 'Induction of persistent tolerance to urushiol in humans.' 68(1):20-25, 1981.*
Epstein et al. 'Poison Oak Hyposensitization: evaluation of purified urushiol.' Arch. Dermatol. 109(3):356-360, 1974.*
Epstein WL, Baer H, Dawson CR & Khurana RC: Poison Oak Hyposensitization, Evaluation of Purified Urushiol. Arch Dermatol Mar. 1974;109(3):356-60.
Epstein WL, Byers VS, Frankart W.: Induction of antigen specific hyposensitization to poison oak in sensitized adults. Arch Dermatol. Sep. 1982;118(9):630-3.
Watson ES, Murphy JC, Wirth PW, Waller CW, & Elsohly MA: Immunologic Studies of Poisonous Anacardiaceae: I. Production of Tolerance and Desensitization to Poison Ivy and Oak Urushiols Using Esterified Urushiol Derivatives in Guinea Pigs . J Invest Dermatol Mar. 1981;76(3)164-170.
Watson ES, Murphy JC & Elsohly MA: Immunologic Studies of Poisonous Anacardiaceae: Oral Desensitization to Poison Ivy and Oak Urushiols in Guinea Pigs. J Invest Dermatol Mar. 1983;80(3): 149-155.
Walker LA, Watson ES & Elsohly MA: Single Dose Parenteral Hyposensitization to Poison Ivy Urushiol in Guinea Pigs. Immunopharmacology and Immunotoxicology 1995;17(3),565-576.
Marks JG Jr, Trautlein JJ, Epstein WL, Laws DM, Sicard GR: Oral hyposensitization to poison ivy and poison oak. Arch Dermatol. Apr. 1987;123(4):476-8.
Hans J. Maasch and David G. Marsh, Standardized extracts modified allergens-allergoids, Clinical Reviews in Allergy and Immunology, 1987;5(1):89-106.
Tams JW, Vind J, Welinder KG: Adapting protein solubility by glycosylation: N-Glycosylation mutants of Coprinus cinereus peroxidase in salt and organic solutions, Biochimica et Biophysica Acta—Protein Structure and Molecular Enzymology, 1999; 1432(2):214-221.
Marks JG;Fowler JF;Sheretz EF;Rietschel RL: Prevention of Poison Ivy and Poison Oak Allergic Contact Dermatitis by Quaternium-18 Bentonite. J Am Acad Dermatol Aug. 1995;33(2 Pt 1):212-6.

* cited by examiner

*Primary Examiner* — Nora Rooney
(74) *Attorney, Agent, or Firm* — Kristina Castellano; Castellano PLLC

(57) ABSTRACT

Provided are compositions that include one or more natural, recombinant and/or modified allergens; with a pharmaceutically acceptable non-aqueous solvent to form an immunotherapy composition that includes the active ingredient and solvent, wherein the immunotherapy composition is formulated for administration to a subject in need of immunotherapy. The solvent is miscible with water and interstitial fluid. The at least one active ingredient is soluble in the solvent and insoluble in water and in an aqueous phase of interstitial fluid. The present compositions may be administered to a patient for example, as part of an immunotherapy regimen to help induce a state of immunologic tolerance to one or more allergies, or as treatment for an autoimmune disease. Also provided are methods of making such compositions. Further provided are methods that include administering the composition to a mammal.

3 Claims, 1 Drawing Sheet

Poison Ivy Immunotherapy tables

Table 1   Marks reaction scale modified by addition of grade 8   Interpolation

| Grade ≤ 7 days | | Factor |
|---|---|---|
| 0 | No reaction | |
| +/- | Questionable reaction (erythema, with or without edema, without itching) | |
| 1 | Erythema with itching | |
| 2 | Erythema with edema and itching | 1.5 |
| 3 | Erythema, edema, and beginning vesiculation involving less than 25% of the test site | 1.0 |
| 4 | As in 3+, but vesicles involving 25% to 50% of the treatment site | 0.7 |
| 5 | As in 3+, but vesicles involving 50% to 75% of the treatment site | 0.45 |
| 6 | As in 3+, but vesicles confluent in a circular pattern on the test site | 0.3 |
| 7 | Erythema, edema, vesiculation, and evidence of ulcerative breakdown | 0.2 |
| 8 | Distant patches of mild-moderate poison ivy dermatitis at old natural contact reaction sit | 0.2 |

Table 2   Response to PI immunotherapy

| Pt # | 1 | 2 | 3 | 4 | |
|---|---|---|---|---|---|
| Sex + Age | M-69 | M-30 | F-57 | F-15 | |
| Severity | Mild | Severe | Moderate | Severe | |

Baseline

| + Patch | F1 | F2 | F2 | F3 | Strength of patch test => reaction ≥ grade 3 |
|---|---|---|---|---|---|
| Max Score | 6 | 8 | 3 | 5 | Grade of that reaction |
| Interp grade 3 | 3 ul F1 | 2 ul F2 | 10 ul F2 | 4.5 ul F3 | Interporated vol/strength needed for grade 3 |
| ug Urushiol | 0.339 | 0.0226 | 0.113 | 0.00509 | ug urushiol in patch to => grade 3 |

| Cum dose-1 | 49 | | 163 | 163 | Cumulative dose at this point in Tx (ug) |
|---|---|---|---|---|---|
| x base gr 3 | 144.54 | | 1,442.48 | 32,023.58 | Cum dose as multiple of baseline grade 3 patch |
| + Patch | F1 | | F2 | F3 | Strength of patch test => reaction ≥ grade 3 |
| Max Score | 6 | | 3 | 2 | Grade of that reaction |
| Interp grade 3 | 3 ul F1 | | 10 ul F2 | 1.5 ul F2 | Interporated vol/strength needed for grade 3 |
| ug Urushiol | 0.339 | | 0.113 | 0.017 | ug urushiol in patch to => grade 3 |
| x less sens | 1.00 | | 1.00 | 3.34 | Current grade 3 patch dose / dose at baseline |

Table 2   - ctn'd

| Cum dose-2 | 840 | 778 | 841 | 841 | Cumulative dose at this point in Tx (ug) |
|---|---|---|---|---|---|
| x base gr 3 | 2,477.88 | 34,424.78 | 7,442.48 | 165,225.93 | Cum dose as multiple of baseline grade 3 patch |
| + Patch | F1 | F1 | F2 | F2 | Strength of patch test => reaction ≥ grade 3 |
| Max Score | 3 | 6 | 3 | 3 | Grade of that reaction |
| Interp grade 3 | 10 ul F1 | 3 ul F1 | 10 ul F2 | 10 ul F2 | Interporated vol/strength needed for grade 3 |
| ug Urushiol | 1.13 | 0.339 | 0.113 | 0.113 | ug urushiol in patch to => grade 3 |
| x less sens | 3.33 | 15.00 | 1.00 | 22.20 | Current grade 3 patch dose / dose at baseline |

| Clin imprvt | (1) | (2) | (3) | (4) | Subjective benefit of Tx (below) |
|---|---|---|---|---|---|

(1)   (The author): Clinical benefit uncertain - still got mild PI from 2009 harvest.
(2)   Complete clinical & patch test remission 9 mos after Tx, relapse of both @ 14 mos.
(3)   Cannot tell if partial control as major contact source, her pet dog, died..
(4)   Initial mod-severe PI from even low dose needle tracks, PI tolerance much improved after Tx

IMMUNOTHERAPY COMPOSITIONS AND METHODS OF TREATMENT

RELATED APPLICATIONS

This application claims the benefit of U.S. Provisional Application No. 61/336,205 filed on Jan. 19, 2010, U.S. Provisional Application No. 61/336,799 filed on Jan. 27, 2010, and U.S. Provisional Application No. 61/398,170 filed on Jun. 22, 2010, the contents of each of which are hereby incorporated herein in their entireties.

FIELD

The present disclosure relates generally to immunotherapy compositions that include one or more natural, recombinant and/or modified allergens and at least one pharmaceutically acceptable non-aqueous solvent that is miscible with water and interstitial fluid. The at least one active ingredient is soluble in the solvent and insoluble in water and in interstitial fluid. The present disclosure also relates to methods of making such immunotherapy compositions, and methods that include administering immunotherapy compositions to a subject to treat an autoimmune disease and/or to induce a state of immunologic tolerance to one or more allergies.

BACKGROUND

Allergic contact dermatitis to urushiol (the allergen in poison ivy) is a common problem for which avoidance is often not practical.

Allergic contact dermatitis to the 15 or 17 carbon alkyl-substituted catechol oils present in poison ivy/oak & sumac and other plants of the Family Anacardiaceae (including cashew nut shells and mango fruit and sap), is a common source of chronic and recurrent morbidity among persons in rural and suburban parts of the eastern and central U.S. Immunotherapy with purified urushiol in olive oil was studied by both the oral route and by intramuscular injection in the 1970's. (Epstein W L, Baer H, Dawson C R & Khurana R C: Poison Oak Hyposensitization, Evaluation of Purified Urushiol. Arch Dermatol 1974 March; 109(3):356-60). Intramuscular (IM) injections were reported not tolerated because of local itch and rash, though the dose causing the reactions was not stated. Oral immunotherapy at cumulative doses of 100-677 mg reduced quantitative patch test reactivity but did not eliminate it, with loss of effect in the absence of weekly maintenance therapy. There were no treatment-associated abnormalities in CBC, urinalysis or basic blood chemistry and adverse effects were limited to transient, mild poison ivy-like eruptions in various body locations. These were controlled by "dose adjustment."

Hyposensitization but not total loss of reactivity, persisting for 3 months without continuing maintenance therapy, was observed in 15 of 21 human subjects receiving a cumulative oral dose of 300 mg of the same formulation in a follow-up study. (Epstein W L, Byers V S, Frankart W.: Induction of antigen specific hyposensitization to poison oak in sensitized adults. Arch Dermatol. 1982 September; 118(9):630-3.)

The Hartley guinea pig can be sensitized to poison ivy and has been used as an animal model for poison ivy immunotherapy. ElSohly et al studied the immunotherapeutic response to diacetate esters of first natural and then synthetic poison ivy and poison oak urushiols in the Hartley guinea pig, his rationale being that the diacetate esters are "less toxic" on administration (by which he appears to mean less likely to provoke acute allergic contact dermatitis). He proposed that the esters are hydrolyzed by cell membrane esterases to release free and biologically active urushiol at sites at which it will be immunotherapeutic, so that one can deliver effective treatment doses more rapidly and eliminate the gradual build-up needed for immunotherapy with unesterified urushiol. He documented the effectiveness of 100 mg/Kg doses of urushiol given IV to guinea pigs as the diacetate ester in Arlacel emulsion, (Watson E S, Murphy J C, Wirth P W, Waller C W, & Elsohly M A: Immunologic Studies of Poisonous Anacardiaceae: I. Production of Tolerance and Desensitization to Poison Ivy and Oak Urushiols Using Esterified Urushiol Derivatives in Guinea Pigs. J Invest Dermatol 1981 March; 76(3)C64-70). He reported efficacy of the same dose of urushiol diacetate dissolved in corn oil and given by mouth, (Watson E S, Murphy J C & Elsohly M A: Immunologic Studies of Poisonous Anacardiaceae: Oral Desensitization to Poison Ivy and Oak Urushiols in Guinea Pigs. J Invest Dermatol 1983 March; 80(3): 149-55) and of 20 mg urushiol diacetate given IM in corn oil given either as a single dose or divided into 3 doses. (Walker L A, Watson E S & Elsohly M A: Single Dose Parenteral Hyposensitization to Poison Ivy Urushiol in Guinea Pigs. Immunopharmacology and Immunotoxicology 1995; 17(3), 565-576.) A mix of diacetate esters of poison ivy and poison oak urushiols given by mouth did not reduce quantitative patch test sensitivity at cumulative doses of either 306 mg or 1266 mg in poison ivy or poison oak-allergic humans. (Marks J G Jr, Trautlein J J, Epstein W L, Laws D M, Sicard G R: Oral hyposensitization to poison ivy and poison oak. Arch Dermatol. 1987 April; 123(4):476-8).

SUMMARY

The present inventor has discovered superior compositions and methods for delivering various allergens with appropriate solubility properties, whether native such as urushiol, or modified such as the peanut allergoids, in a suitable solvent to e.g., facilitate the development of T-cell tolerance by presenting the vaccine to the immune system in the form of large numbers of small insoluble particles deposited by precipitation in richly vascularized muscle. For allergens for which it is possible to prepare allergoids with the solubility properties needed for delivery by the present methods, there may be a synergistic benefit from the combination of the chemical modification of making the allergoid and the physical effect of the present method of composition or vaccine delivery.

The present disclosure relates generally to immunotherapy compositions that include one or more natural or recombinant autologous or foreign tissue antigens and/or their derivatives, e.g., modified allergens (including allergoids), and at least one pharmaceutically acceptable non-aqueous solvent, including, but not limited to, ethanol, ethyl acetate, acetonitrile and dimethylsulfoxide. The present compositions may be administered to a subject (such as a mammal) for example, as part of an immunotherapy regimen to help the subject induce a state of immunologic tolerance to one or more allergies. According to non-limiting example embodiments, natural or recombinant autologous antigens and their derivatives may be administered for the treatment of autoimmune diseases. Thus, the present disclosure also relates to methods that include administering the immunotherapy composition to the subject. According to non-limiting embodiments, the composition is administered intramuscularly. The present application further relates to methods of making immunotherapy compositions disclosed herein.

Also included herein are compositions that include at least one natural or recombinant allergen and/or modified allergen and at least one pharmaceutically acceptable non-aqueous solvent, that are formulated for the treatment of autoimmune disease in a subject, by inducing T-cell immunologic tolerance in the subject. The present application also encompasses methods of making these compositions and methods of treating a subject by administering such compositions to the subject.

Further provided are compositions and methods that may utilize the compositions provided herein as a delivery system for additional active ingredients.

BRIEF DESCRIPTION OF THE DRAWINGS

Illustrative embodiments of the present disclosure are herein described, by way of non-limiting example, with reference to the following accompanying FIGURE:

FIG. 1, Table 1 depicts a reaction scale along with an Interpolation factor, for determining quantitative grading of patch test reactivity in allergic contact dermatitis. Table 2 depicts response to PI immunotherapy for each of the subjects in Example 1 herein.

DETAILED DESCRIPTION

The present inventor has discovered that particular immunological compositions and methods of allergy vaccine delivery have safely produced clinically effective immunologic tolerance to an allergen, for which no previous efforts at immunotherapy have been predictably or reproducibly effective. It is believed that similar methods of allergy vaccine delivery could be adapted to numerous other allergic conditions and that it might be similarly efficacious for those conditions. It is also believed that this method of delivery of a therapeutic agent to the body may have applications outside of allergen immunotherapy.

Generally provided herein are immunotherapy compositions and methods that provide immunotherapy for inducing a state of immunologic tolerance to an allergen. Such tolerance may act to reduce and/or prevent future allergic reactions in a subject (such as mammals), which allergic reactions are generally caused by exposure of the subject to an allergen. By way of example, present embodiments include compositions and methods of treating a subject by administering compositions to the subject, wherein the compositions include one or more allergens (such as natural or recombinant allergens, or modified allergens, including derivatives of each) and at least one pharmaceutically acceptable non-aqueous solvent. The at least one active ingredient is soluble in the solvent and insoluble in water and interstitial fluid. The solvent is miscible with water and interstitial fluid. Also included are methods of making the present immunotherapy compositions, and methods of administering these compositions to a subject. Thus, the present compositions and methods may be useful for example, in reducing or eliminating a patient's allergic response to exposure to an allergen such as those in peanuts, stinging insect venoms, latex, tissue, and the like.

Various formulations and methods for allergen immunotherapy have enabled the generally safe and effective induction or enhancement of immunologic tolerance in numerous allergic conditions. These treatments are sub-optimal or not available for many allergic diseases, however. The present inventor has discovered that when an allergen is formulated with a suitable solvent as set forth herein and administered as set forth herein, the allergen has unexpectedly superior effects inducing a state of immunologic tolerance to the allergen. Thus, the present compositions and methods provide a previously undiscovered and safe method of treating an allergic patient.

The aspects, advantages and/or other features of example embodiments of the present disclosure will become apparent in view of the following detailed description, taken in conjunction with the accompanying drawings. It should be apparent to those skilled in the art that the described embodiments of the present disclosure provided herein are merely exemplary and illustrative and not limiting. Numerous embodiments of modifications thereof are contemplated as falling within the scope of the present disclosure and equivalents thereto. Unless otherwise noted, technical terms are used according to conventional usage. All patents and publications mentioned in this specification are indicative of the level of those skilled in the art to which the invention pertains. All publications, patent applications, patents, and other references mentioned herein are incorporated by reference in their entirety.

In describing example embodiments, specific terminology is employed for the sake of clarity. However, the embodiments are not intended to be limited to this specific terminology.

As used herein, "a" or "an" may mean one or more. As used herein, "another" may mean at least a second or more. Furthermore, unless otherwise required by context, singular terms include pluralities and plural terms include the singular.

The term "antigen" as used herein is a substance capable of eliciting a specific response by the immune system of an exposed animal or human. An antigen is an allergen when the specific immune response is the development or modification of an allergy to that substance.

As used herein, "composition", "therapeutic composition", "immunotherapy composition" and "formulation" may be used interchangeably and refer to a combination of elements that is presented together for a given purpose. Such terms are well known to those of ordinary skill in the art.

The terms "active ingredient" and "drug" are used herein to include any drug or active ingredient that may be included in the present compositions for treating subjects, including mammals.

According to non-limiting embodiments, the active ingredient may be used in an effective amount to treat a disorder of either deficient or excessive immunologic tolerance. Non-limiting example embodiments of natural or recombinant allergens that may be included in the formulation include for example, plant allergens (e.g., poison ivy); food allergens (e.g., peanut, milk, egg, peanut, tree nuts, fish, shellfish, wheat, and soy); insect-derived allergens; inhalant airborne allergens (e.g., to treat respiratory allergies); contact allergens; latex allergens; chemical and biological allergens (which cause e.g., allergic contact dermatitis), tissue allergens, drug allergens; modified versions of such allergens, and synthetic equivalents of such allergens. According to other example embodiments, "active ingredients" may also include one or more additional or different ingredients than those listed above, such as one or more other allergens, other modified allergens, non-allergens or synergistic ingredients that may be used to treat a mammal or other subject (such as avian) in need of treatment.

Encompassed by the term "active ingredients" and/or included with in the meaning of "allergen" as provided herein, are natural or recombinant allergens, modified allergens and both natural and synthetic allergens, or any other variation of any allergens, or similar ingredient that may provide the same or similar active components as the indicated active ingredient. According to non-limiting example embodiments, active ingredients may include one or more natural or recombinant autologous or foreign tissue antigens or their derivatives for the treatment of autoimmune diseases.

According to non-limiting example embodiments throughout this application, the at least one pharmaceutically acceptable active ingredient, may be at least one of tissue or modified tissue antigens.

Although examples embodiments herein were performed using natural allergens, it is contemplated by the inventors that synthetic allergens may be used, and therefore, they should be deemed encompassed by all the present invention. One may be able to make for example, a more concentrated and highly purified solution of urushiol synthetically than by concentrating and purifying it from natural poison ivy. The use of natural products may be advantageous for certain allergens under certain circumstances. Natural poison ivy may be used to produce a supply of a more concentrated partially purified urushiol vaccine that can be used to treat patients.

Recombinant DNA technology allows natural, modified or totally synthetic segments of genetic code to be inserted into organisms to which they are not native, usually specific strains of bacteria, which can be induced to produce any protein(s) coded by the transplanted genetic code. When such proteins are allergens, mutant versions which may have altered allergenicity and potential value as materials for the production of allergy vaccines can be produced by such measures as exposing their carrier bacteria to chemical mutagens or ionizing radiation. Allergens produced by recombinant DNA technology will be termed "recombinant allergens" whether or not their DNA has been modified from that of the natural allergens, and recombinant allergens which are further modified by physical or chemical means after synthesis will be termed "modified recombinant allergens." Any or all of these as well as allergens produced by methods to be developed in the future may be candidates for enhancement or further enhancement of their immunologic properties by means of the present invention.

The term "excipient" is used herein to include pharmaceutically acceptable inert substances added to a drug formulation or composition to give e.g., a desired consistency or form, or used as a carrier. Non-limiting examples of excipients that may be included in the present compositions and/or formulations herein may include, but are not limited to binders, fillers, diluents, lubricants, anti-infectious agents, antimicrobial agents and solubility modifiers, and other excipients known to those skilled in the art, depending e.g., on the composition being formed, intended method of administration and/or method of formation, the active ingredient(s) being used, etc. When using excipients however, one must keep in mind that traditional excipients may alter the solubility of the solvent and/or active ingredient, thereby altering the suitability and effectiveness of the present compositions and methods. For example, the viscosity of the solvent may need to be low enough that its concentration will rapidly equilibrate with surrounding interstitial or tissue fluid following for example, intramuscular injection into a subject (such as a human). Accordingly, typical excipients, which in other formulations may be used to increase viscosity, may be unsuitable for the present compositions.

As used herein, "an effective amount" refers to an amount of the specified constituent in a composition, or an amount of the overall composition that is effective in attaining results, the purpose for which the constituent or composition is provided. Therefore, an effective amount of a composition would be an amount suitable for achieving the desired immunotherapy effects in a subject, such as a mammal (e.g., human) to which the present composition is administered.

The terms "interstitial fluid" and "tissue fluid" as used herein are intended to have their common meaning in the art. In particular, "interstitial fluid" (or tissue fluid) is a solution that bathes and surrounds the cells of multicellular animals.

As used herein, the term "subject" or "patient" is intended to include any animal, such as a mammal (including, but not limited to humans) to whom the present compositions may be administered. A subject or patient may or may not be under current medical care, and may or may not have had one or more prior treatments. As would be apparent to those skilled in the art, the formulations and dosages may be different for non-humans than for humans, taking into consideration certain solvent requirements are provided herein for safety for injection.

Additional example embodiments, the present invention (compositions, methods, etc) may include compositions and methods for the treatment of birds. Accordingly, example embodiments are directed to compositions and methods for avian use as well.

According to example embodiments, the composition should be miscible with water. It would be apparent to those skilled in the art that vaccines relevant to veterinary use and determined by appropriate regulatory authorities to be safe and effective for such use may be different than vaccines relevant to and determined to be safe and effective for human use. Also, solvents and any other additives determined to be pharmaceutically acceptable for veterinary use may differ from those determined to be pharmaceutically acceptable for human use.

Example embodiments are directed to immunotherapy compositions that include at least one pharmaceutically acceptable active ingredient selected from the group consisting of a natural or recombinant allergen and a modified allergen (which terms are all intended to include derivatives thereof) and at least one pharmaceutically acceptable non-aqueous solvent. The solvent is miscible with water and interstitial fluid. The at least one active ingredient is insoluble in water and in interstitial fluid (e.g., of the subject or patient to whom the composition will be administered), and soluble in the solvent.

The compositions herein may be used for the immunotherapy treatment of autoimmune disorders in a subject such as mammals. According to other embodiments, the compositions herein may be used as a booster of the protective immune response, which may help build a tolerance to allergens and decrease or eliminate the subject's further allergic reactions to the allergen.

According to non-limiting example embodiments, compositions provided herein may include one or more active ingredients (that is a natural or recombinant allergen, or modified allergen), and a non-aqueous solvent. According to example embodiments, as discussed herein, the active ingredient may be at least one natural or recombinant allergen or modified allergen, selected from plant allergens (e.g., poison ivy); food allergens (e.g., peanut); insect-derived allergens (e.g., hymenoptera venoms); inhalant airborne allergens; contact allergens; latex allergens; chemical and biological allergens including tissue allergens; drug allergens; modified versions of such allergens, including derivatives, and synthetic equivalents of such allergens. According to further non-limiting example embodiments, the allergen may comprise one or more of the following, poison ivy allergens; peanut allergens; insect venom allergens; latex allergens and tissue allergens, which may be natural or synthetic, and which include derivatives or modifications thereof.

Derivatives or modified allergens within the scope of the present invention may include for example "allergoids." Marsh and associates (Hans J. Maasch and David G. Marsh, Standardized extracts modified allergens-allergoids, Clinical Reviews in Allergy and Immunology, 1987; 5(1):89-106,) have converted 101 p 1 (rye Group I), the major allergenic component of *Lolium perenne* (rye grass) pollen, into various "allergoid" derivatives by using mild formalin treatment. An allergoid is defined as a "derivative of an allergen having a greatly reduced allergenic reactivity compared with the native allergen from which it was derived, while retaining to a high degree other desirable properties characteristic of the native allergen, including the capacity to induce a synthesis of allergen-neutralizing IgG-blocking antibodies in animals and humans and to protect atopic subjects from experiencing allergic symptoms following allergen exposure." The IgG-blocking antibodies described by Maasch and Marsh are produced in the course of what we now know to be T-cell tolerance induction in diseases in which the disease is mediated by IgE allergic antibody. Whether IgG-blocking antibody is produced in T-cell tolerance induction in diseases of overactive cell-mediated immunity like poison ivy is not known. There are numerous ways in which chemically different allergens (there being potentially relevant carbohydrate allergens as well as protein allergens, for example) could be discovered that have appropriate solubility properties for this invention in their native state (such as urushiols), or else they could be chemically modified to impart them.

The potential of allergoids in the immunotherapy of allergic diseases is based on the theoretical premise that they could be administered in high dosages with negligible risk of systemic reactions and with concomitant immunologic protection against allergic symptoms.

According to non-limiting example embodiments the allergoids may be polymers of allergenic molecules formed by cross-linking an allergen with at least one of glutaraldehyde and formaldehyde. The allergoids may further include one or more adsorbents and/or hydrophyllic or hydrophobic side chains to confer the appropriate solubility properties. Allergoids may also be produced by other means known to those skilled in the art to be capable of reducing the ratio of allergenicity to immunogenicity of the parent allergens.

Allergoids may also include polymers of allergenic molecules with certain additional features. In the case of pollen, for example, allergotropins were produced basing on conjugation of pollen allergoids and polyelectrolite with immunomodulating properties. Pollen allergotropins were designed to treat pollenosis caused by sensitization to timothy and birch pollen.

To give water soluble protein allergens such as the major peanut allergen, Ara h2, the water-insolubility needed for the present vaccine delivery technique, the present inventor elected to pair the vaccine delivery system covered by the present patent application with a method of reducing allergenicity while retaining immunogenicity (in this case tolerogenicity, where the desired immune response is the induction of T cell tolerance). This is the polymerization of molecules of the water-soluble protein allergen by cross-linking with glutaraldehyde and/or formaldehyde to form water-insoluble "allergoids."

Allergoid vaccines were studied for various inhalant allergens in the 1980's and early '90's and were injected subcutaneously where they functioned as slowly released depots of vaccine. Use of allergoid technology to create the solubility properties needed for the technology of the present invention may offer a doubly enhanced ratio of tolerogenicity to allergenicity because of synergy between the two steps.

The solubility properties of allergoids may be modified by various means. The inventors' plan was to first make a number of Ara h2 allergoids of different molecular size and degree of cross-linking, examine their "as-is" solubility properties (expecting most to be insoluble in both water and 95% ethanol) and then modify them by N-glycosylation (Tams J W, Vind J, Welinder K G: Adapting protein solubility by glycosylation: N-Glycosylation mutants of *Coprinus cinereus* peroxidase in salt and organic solutions, Biochimica et Biophysica Acta—Protein Structure and Molecular Enzymology, 1999; 1432(2):214-221) or other means to render them soluble in ethanol while still insoluble in water and other aqueous media.

Latex is a contact allergen capable of causing the same type of allergic contact dermatitis produced by poison ivy. It is different and essentially in a class by itself in its ability to first elicit poison ivy-like allergic contact dermatitis and then (with continuing exposure to the increased numbers of allergen processing cells in the cytokine milieu of the allergic contact dermatitis reaction) stimulate an IgE anaphylactic humoral antibody response, like that of severe food or insect sting allergy. There are probably other chemical entities capable of causing a similar combination of sensitivities in genetically susceptible individuals but none whose widespread use and high frequency of susceptibility has made them public health problems on a scale anywhere near that of latex.

The present compositions and methods may also be used to treat individuals allergic to stinging insect venoms or having other insect related allergies, for example, by administering the present compositions, including "insect-derived allergens" (such as insect venom allergens) to an individual having the insect allergy. Hymenoptera is the order of Class Insecta that includes sawflies, wasps, bees, and ants. Thus, the present invention may include treatment of allergies to insect venom (e.g., from yellow jackets) in the present compositions and methods.

Pharmaceutically acceptable non-aqueous solvents according to the present invention may include for example one or more solvents selected from the group consisting of ethanol, ethyl acetate, acetonitrile, dimethylsulfoxide (DMSO), and other water-miscible solvents. The term "non-aqueous solvent" as used herein is something that isn't water and that because it has different properties of molecular stabilization and surface energy than water is capable of dissolving various substances of interest (such as urushiol for ethanol) that are insoluble in water. With respect to ethanol, for example, whether the ethanol is 65% or 95% or 100% doesn't matter if it is still capable of dissolving the substance of interest. Percent ethanol will matter in that increasing percent water will increasingly confer the surface energy properties of water onto the resulting mixture, reducing the net solubility of water-insoluble components like urushiol.

The amount and type of solvent may depend on what it takes to prepare the active ingredient in a desired/appropriate form with appropriate solubility properties for successful administration/treatment, as could be determined by one skilled in the art. Additionally, according to non-limiting example embodiments the solvent may have a low enough viscosity to achieve rapid equilibration with interstitial or tissue fluid. Water-miscible viscous solvents such as glycerol may equilibrate with interstitial or tissue fluid so slowly that the allergen would precipitate in much smaller numbers of much larger particles, which may have a different effect on the immune system.

According to non-limiting example embodiments, the solvent is ethanol. Previously, ethanol was available in an amount of 95% or less. But it is now possible to purchase pharmaceutical grade anhydrous 100% ethanol, which may also be an acceptable vehicle for the allergens in the present compositions. According to other non-limiting example embodiments, the solvent may be ethyl acetate or other non-aqueous solvents.

In referring to "pharmaceutically acceptable" solvents, Applicants intend to encompass (1) solvents that meet appropriate regulatory criteria for safe use in humans or animal recipients of vaccine or drug to be delivered by the present methods; and (2) solvents which are readily miscible with water and interstitial fluid, which is a solution of certain water-soluble proteins and carbohydrates in physiologic saline. Whether or not a solvent would be considered "pharmaceutically acceptable" may be determined by those skilled in the art, depending for example on the type and amount of the solvent. For example, some solvents may be considered pharmaceutically acceptable in small amounts, but would not be considered pharmaceutically acceptable if administered in large amounts.

The present inventor has surprisingly found that intramuscular injection such a formulation into mammals, and in particular, humans, provides unexpectedly superior induction of tolerance to e.g., poison ivy, an allergen causing T-cell mediated allergic contact dermatitis, leading to the present invention as a way to induce tolerance to any allergic condition mediated by the same T-cell immune mechanism.

This finding was surprising, as compared to published data from mammalian systems. For example, urushiol injected IM in small volumes of 95% ethanol was 200 times as effective in immunotherapy dose per unit body weight of the recipient as urushiol dissolved in corn oil, which is not waster miscible and for that reason not immediately diluted by interstitial or tissue fluid to precipitate large numbers of small particles of insoluble antigen in muscle.

A vaccine or drug or active ingredient to be delivered (such as the allergen) should be soluble in the water-miscible solvent but insoluble in water and in the solution of proteins and carbohydrates in physiologic saline that comprises interstitial or tissue fluid.

By way of non-limiting example, the solvent(s) may be included in the composition/formulation as remaining solvent after an extraction of the allergen (such as poison ivy) using the solvent. According to alternative embodiments, the solvent may be added to an allergen after extraction, or in the case of synthetically produced allergens, the solvent may simply be added to the allergen.

As discussed above, one or more pharmaceutically acceptable excipients may be used in the present compositions in accordance with the present application, for example for administration purposes and/or to help the allergen achieve desired properties, so long as the excipients do not alter the required physical characteristics (such as solubility) of the active ingredient and/or solvent. Other potential pharmaceutically acceptable carriers or components may also be added to the formulation depending on what it takes to get drug or vaccine into a form with appropriate solubility properties.

Accordingly, example compositions may include one or more excipients that may be selected, for example based on the type of composition being formed, desired route of administration and properties to be achieved, etc. A goal of the present method is to have the drug become insoluble as quickly as possible, as the water-miscible solvent in which it is injected (for example, 95% ethanol) is rapidly diluted by interstitial or tissue fluids. This results in the precipitation of much larger numbers of much smaller particles with a much larger total surface area than if the ethanol concentration was allowed to fall more slowly. Rapid dilution of solvent appears to be important for the effective operation of the present compositions and methods. Accordingly, any excipients added to the compositions should not alter these properties.

According to non-limiting example embodiments, the composition may be a combination formulation with more than one natural or recombinant allergen and/or modified allergens, including their derivatives, which may be used to simultaneously treat autoimmune disease and/or multiple allergies with each dose. In said combination therapies, the respective manufacturing processes and chemical environments would have to be compatible with one another. Example compositions may be quite useful in being able to provide a combination therapy composition for the treatment of at least two different allergies in a single shot or other dosage form. According to non-limiting example embodiments, the present immunotherapy compositions may include at least two different active ingredients selected from the group consisting of natural allergens, recombinant allergens, and modified allergens, to provide a combination therapy composition for the treatment of at least two different allergies or other conditions. Multiple allergens may be administered in a single dose if their preparation process and solvent requirements are mutually compatible.

The present compositions may further include one or more pharmaceutically acceptable active ingredients that are not an allergen, in addition to the allergens, solvent and/or additional ingredients. Such active ingredients may include for example other treatments for allergies or autoimmune disorders that may be delivered via the present compositions. These active ingredients may for example, treat allergy symptoms or autoimmune symptoms, without necessarily triggering an immune response.

Foreign materials introduced into the body, whether immunologically active, pharmacologically active, metabolically active, toxicologically active or inert, are processed differently depending on the site, route, form and dose in which they are administered. The present inventor interprets the unexpectedly favorable processing of e.g., poison ivy allergen (described further below) when injected IM in ethanol to result from the rapid precipitation of large numbers of very small particles with a large surface area in intimate contact with interstitial fluid. At this point it is not clear if the observed effect results from persistence of small insoluble particles in situ or their being of an appropriate size and accessibility to antigen-processing cells to be taken up and transported into lymph nodes. Applicant notes that the final percent of ethanol was unknown, less than 95% because of the water content of the fresh poison ivy leaves, and it was probably further decreased the initial attempt to concentrate the active ingredient by preferential evaporation of ethanol in the reduced pressure heated evaporation process that was used for concentration. Control of the water content of the solvent is therefore believed to be an important aspect of the present compositions and methods.

As previously indicated, the solubility properties of the present composition are of utmost importance in preparing a suitable formulation. Thus, the present compositions may include adding adsorbents or side chains to the allergens or allergoids to confer appropriate solubility properties. According to example embodiments, the at least one natural or recombinant allergen and/or modified allergen may be capable of precipitating insoluble particles after injection of the immunotherapy composition into a subject. Additionally, the present application is intended to include other physical or chemical modifications known to those skilled in the art or that may be discovered in the future to alter the solubility properties of substances or their derivatives with antigenic activity, in view of the present disclosure. Trosine adsorption is an example of a non-covalent modification capable of changing the solubility properties of certain proteins including certain protein allergens.

According to non-limiting example embodiments the present compositions or formulations may be in e.g., a liquid formulation suitable for injection, such as intramuscular, subcutaneous, intradermal, or intraperitoneal injection, or it may be in a formulation that is suitable for administration by other routes, e.g., topical. Although intramuscular (IM) formulations are presently preferred, particularly for human applications, it is possible that other routes of administration may be suitable as well. Intraperitoneal injection might be an effective means of allergen delivery in small laboratory animals, though intraperitoneal injection in animals is generally used to induce the production of specific types of antibody rather than to induce tolerance. Other possible formulations may include liquid, powders, or other formulations that may be suitable for e.g., various types of injection or topical administration.

By way of example, a powdered formulation could be lyophilized and redissolved in a pharmaceutically acceptable solvent for injection. It is also possible that some solvents, possibly DMSO, could diffuse away rapidly enough to produce sufficiently rapid precipitation following subcutaneous injection to yield particles of precipitated allergen of appropriate size. DMSO penetrates skin following topical application and could carry enough of a dissolved drug to penetrate to a medically significant degree before the DMSO is diluted sufficiently to precipitate the allergy vaccine or other drug it contains. One may not expect this to be an efficient method of immunotherapy for conditions in which the pathophysiology includes allergic contact dermatitis (like poison ivy or latex allergy), as immune system entry via processing by antigen-processing cells in the skin is the mechanism by which these diseases develop in the first place. However, there are enough switch points in the immune system at which high doses and low doses of allergen have opposite effects, so that the inventor can not rule out the possibility that this method of delivery of an allergy vaccine would necessarily be ineffective or less effective than IM administration. With that in mind, topical administration may be expected to be relatively more useful for allergies for which the disease mechanism does not involve allergic contact dermatitis.

Thus, it is possible that the present compositions and methods might be effective when administered in ways other than IM administration, for example, either by topical application in DMSO (for example) or by intradermal injection. According to example embodiments, such methods may be used not to create immunologic tolerance but to create immunologic sensitization to tumor antigens in cancer patients who are immunologically unreactive to their cancers. The mechanism would again be deposition of large numbers of small particles as the solvent is diluted by what in this case would be interstitial fluids of the dermis (deeper living layer of the skin) and possibly superficial subcontaneous tissue. This could work if the mechanism of action of urushiol tolerogenesis is not subcutaneous persistence of small insoluble particles but their uptake by antigen processing cells of the immune system. In skin, where antigens are processed by a different set of cells called Langerhans cells which in many circumstances promote sensitization rather than tolerance, the outcome of precipitation of critically sized particles from solvent could be sensitization rather than tolerogenesis.

Example embodiments are also directed to methods of making the compositions or formulations herein.

According to non-limiting example embodiments, methods of making an immunotherapy composition may include extracting at least one pharmaceutically acceptable active ingredient selected from the group consisting of natural, recombinant, and modified allergens, including derivatives of each; with a pharmaceutically acceptable non-aqueous solvent such as e.g., ethanol or ethyl acetate, to form a composition comprising the extracted active ingredient and solvent. The composition should be formulated such that it is suitable for injection into a subject in need of immunotherapy. The solvents and active ingredients are as discussed with respect to the compositions herein. Thus, the solvent is miscible with water and interstitial fluid, and the at least one active ingredient is soluble in the solvent and insoluble in water and in interstitial fluid.

As discussed above, the pharmaceutically acceptable active ingredient may include at least one ingredient selected from the group consisting of plant allergens; food allergens; insect-derived allergens; inhalant airborne allergens; contact allergens; latex allergens; chemical and biological allergens such as tissue allergens; drug allergens; modified versions of such allergens; and synthetic equivalents of such allergens.

According to further non-limiting example embodiments, methods of making an immunotherapy composition may include combining at least one pharmaceutically acceptable active ingredient selected from the group consisting of a natural, recombinant, and modified allergens; with a pharmaceutically acceptable non-aqueous solvent to form an immunotherapy composition comprising the active ingredient and solvent. The immunotherapy composition is formulated for administration (e.g., by injection, topical administration, etc) to a subject in need of immunotherapy. The solvents and active ingredients are as discussed with respect to the compositions herein. Thus, the solvent is miscible with water and interstitial fluid, and the at least one active ingredient is soluble in the solvent and insoluble in water and interstitial fluid.

According to non-limiting example embodiments the pharmaceutically acceptable active ingredient is a modified allergen or allergoid; and the modified allergen may be formed by modifying an allergen by cross-linking the allergen with glutaraldehyde and/or formaldehyde.

The pharmaceutically acceptable active ingredient in these embodiments may include one of those previously set forth herein and in particular may include at least one ingredient selected from the group consisting of plant allergens; food allergens; insect-derived allergens; inhalant airborne allergens; contact allergens; latex allergens chemical and biological allergens such as tissue allergens; drug allergens; synthetic equivalents of such allergens; and modified versions of such allergens.

Further methods encompassed by the present invention may include polymerizing a metabolic precursor of an active ingredient and coupling said polymerized metabolic precursor to at least one natural or recombinant allergen or modified allergen for administration to a patient having an allergy to the allergen. These methods may further include for example administering the polymerized metabolic precursor and allergen or modified allergen to the patient who is allergic to the allergen.

The present application is further intended to encompass any other therapeutic agent or combination of agents for which the present route of delivery to the body enhances effectiveness, reduces adverse effects, or both. By way of example, if one wants to treat some type of cancer of the immune system with a locally acting drug, the present delivery compositions and methods may be a potentially effective way to deliver it to be polymerize a metabolic precursor of the drug and couple it to an allergen to which the patient is allergic and then inject it by the present methods so it's taken up by cells of the desired target tissue inside of which the drug is activated and kills them. Such methods, compositions and uses are intended to be encompassed hereby.

The present application is also directed to methods that include administering to a subject having an allergy or autoimmune condition, an immunotherapy composition provided herein. For example, the immunotherapy composition may include at least one pharmaceutically acceptable active ingredient selected from the group consisting of natural allergens, recombinant allergens and/or modified allergens; and at least one pharmaceutically acceptable non-aqueous solvent. As indicated above, the solvent is miscible with water and interstitial fluid; and the at least one active ingredient is insoluble in water and in interstitial fluid, and soluble in the solvent.

As previously indicated, the subject may be a mammal (as well as other animals), and the mammal may be (but does not have to be) human.

By way of non-limiting example, the administering may include injecting the composition into a muscle of e.g., the mammal, but other forms of administration, such as topical administration (e.g., to the skin of a mammal), intradermal injection, or intraperitoneal injection, are encompassed herein as well. According to non-limiting example embodiments, as discussed above, the present compositions may be administered to a mammal by intraperitoneal injection, although the lymphatic drainage from the intraperitoneal space is different and dilution and precipitation might take place at a different rate resulting in a different size distribution of the resulting particles. Even if particle size distributions are similar, allergen precipitated in different tissues might interact with different populations of antigen-processing cells with a different net effect. Intradermal injection may stimulate tumor immunity, e.g., when the composition includes native or modified antigens. According to non-limiting example embodiments the present methods may include administering the present compositions by intradermally injecting the composition into a mammal to stimulate tumor immunity, wherein the composition comprises native, modified, recombinant or synthetic tumor antigens.

According to non-limiting example embodiments, the present compositions and methods help individuals having allergies develop a state of immunologic tolerance to the offending allergen(s), such that if the individual is exposed to allergens, the severity, duration, and/or type of reaction may be diminished or completely alleviated as compared to allergic reactions that may have occurred if the individual had not been treated with the present compositions and methods. As is known to those skilled in the art, the dosages may increase over time as one induces a state of immunologic tolerance.

Appropriate dosages of the compositions provided herein may be determined by those skilled in the art, depending on various factors, such as the severity of the allergy (e.g. previous allergic reactions and potential for severe adverse affect if exposed to the allergen), the weight of the mammal, the type of allergy being treated, etc. Dosage amounts, frequency and total number of doses, may be adjusted to achieve desired affects, depending on for example, the subject's/patient's tolerance and reaction to previous doses (if any). A unit dosage may comprise a therapeutically effective amount of e.g., a natural or recombinant allergen or modification or derivative thereof. A unit dosage will depend upon many factors including age, size, and condition of the individual being treated and the number of times the unit will be taken.

For inhalant allergen immunotherapy sequential doses may be given for example, in clusters with dose increases every 30 minutes for a cluster of usually two or three doses but occasionally, more. Two hours was the originally reported dosing interval when rush immunotherapy was first reported in approximately 1980. Allergists usually do not increase dose at shot intervals greater than 2 weeks during the induction phase of inhalant immunotherapy because of the risk of loss of tolerance. The present inventor conservatively elected to give increasing doses of poison ivy extract at 1-2 week intervals in the immunotherapy of previously untreated patients with poison ivy. Because poison ivy patients are not at risk for the acute severe shot reactions that are possible in inhalant or insect venom immunotherapy, the interval between doses may be much less critical for poison ivy immunotherapy than for immunotherapy to inhalant aeroallergens and stinging insect venoms. For severe food and latex allergy and for many medication allergies there are presently no forms of immunotherapy recognized to be both safe and effective. All of these are potential candidates for the present invention.

Absorption of epinephrine injected for allergic emergencies has been shown to be faster from thigh than from deltoid (upper arm over and just below shoulder). The present inventor has used the deltoid, as it requires less undressing and if the injection site is tender it is generally easier to rest your arm than the leg you walk on.

The present compositions may be used for treating mammals for a variety of different allergies. The present embodiments are generally to be used for inducing a state of immunologic tolerance to allergens that may be most common in humans and/or those that have the greatest potential for severe adverse effect if an allergic reaction were to occur (e.g., peanut allergens, insect sting allergens, etc.). Given that the compositions include an allergen to which the patient is commonly allergic and has the potential for adverse effect, the compositions herein should be administered by a trained physician, preferably in a medical setting in order to minimize the potential for adverse events and to make sure that no other intervention is needed, or provide such intervention if needed.

As indicated above, the allergen, may include genetically modified recombinant allergens. Other classes of allergens may be compatible with different methods to achieve the solubility properties needed for this method of vaccine delivery. In particular, recombinant allergens may include allergens manufactured by transferring the gene for the protein to be manufactured into a strain of bacteria that then produces it in culture. Up to this point there are no known genetically modified recombinant allergens with the solubility properties needed for the vaccine delivery system provided herein, but there is no reason why that could not be done either directly (modifying genes to directly synthesize allergens with the desired solubility properties) or indirectly (modifying genes to synthesize allergens with specific chemical features that would enable or facilitate separate chemical processes to cross-link or otherwise modify them to yield appropriate solubility properties) for the present methods of vaccine delivery.

Example embodiments are also directed to methods of treating an autoimmune disease that include administering to a subject having an autoimmune disease, a composition comprising: at least one pharmaceutically acceptable active ingredient selected from the group consisting of at least one native, natural or recombinant tissue or tissue-related allergen and modified allergen; to induce T-cell immunologic tolerance in the subject (such as a mammal). Administration of such doses may occur anywhere from two hours to two weeks between shots. Corresponding compositions that may be used for the treatment of autoimmune diseases are also encompassed hereby. Each of the ingredients may be as set forth herein with respect to other embodiments.

Further example embodiments may include kits and/or systems that include inter alia, one or more of the compositions provided herein. The kits or systems may further include one or more of the following, or other ingredients typically present in composition kits: instructions for use, injection or other administration implements or devices (such as needles, syringes, vials, disinfectant wipes, etc.), disposable implements, additional treatment literature, additional implements or compositions for the treatment of allergies and/or autoimmune disorders, e.g., antiinflammatories, etc.

The following examples are provided to further illustrate various non-limiting embodiments and techniques encompassed by the present invention. It should be understood, however, that these examples are meant to be illustrative and do not limit the scope of the claims. As would be apparent to skilled artisans, many variations and modifications are intended to be encompassed within the spirit and scope of the present disclosure.

EXAMPLES

Example 1

Summary

Nine hundred grams of fresh poison ivy leaves were extracted with 95% ethanol and evaporated to a concentration of 1.13 mg urushiol/ml. Serial 10-fold dilutions of this concentrate were prepared in 95% ethanol. Five subjects with clinical poison ivy allergy were tested with increasing concentrations using a standardized patch test for which reduction of reactivity was previously accepted by the FDA as proof of the efficacy of a barrier product. Four requested immunotherapy "IT" under a protocol consisting of 3-fold increases in IM dose of the ethanol extract at 1-2 wk intervals beginning with 10× the quantity of urushiol giving a "grade 3" reaction on the standardized patch test, and ending with paired injections of 170 µg into each deltoid repeated once. Toxicity was monitored clinically and by CBC, Diff, multichem and UA performed before, during and following treatment.

One each subject with mild and moderate patch test reactivity and clinical disease demonstrated a 1 to 3-fold reduction in patch test sensitivity following treatment and no change in sensitivity to natural exposure. Two highly allergic subjects demonstrated 15 and 22-fold reduction in patch test sensitivity with complete loss of sensitivity to natural exposure. Response in three subjects studied at two points in their treatment protocol indicated a dose-related response. No adverse effects were observed.

Poison ivy allergy responds to adequate dose immunotherapy using the present compositions.

Materials and Methods:

At the end of the 2008 growing season the inventor harvested 900 grams of fresh poison ivy leaves and performed a crude urushiol extraction by eluting for 4 days with 8 liters of beverage-grade 95% ethanol. A rotary vacuum evaporator was used to concentrate crude extract. Dr. Richard Sicher of the USDA-ARS included samples of the material when performing urushiol assays for other purposes, and determined the urushiol content of the 2008 concentrate to be 1.13 mg/ml. He also assayed the inventor's unconcentrated 2008 and 2009 extracts.

The inventor prepared three 10-fold serial 95% ethanol dilutions (labeled F1, F2 and F3) of the 2008 concentrate (labeled F0) and offered quantitative patch testing and immunotherapy, with informed consent, to patients with chronic or recurrent moderate to severe poison ivy for whom avoidance was not a practical solution. Patch tests with 10 ml volumes of urushiol solution were applied weekly, according to the method of Marks, (Marks J G; Fowler J F; Sheretz E F; Rietschel R L: Prevention of Poison Ivy and Poison Oak Allergic Contact Dermatitis by Quaternium-18 Bentonite. J Am Acad Dermatol 1995 August; 33(2 Pt 1):212-6) beginning with F3 for highly sensitive individuals and with F2 and F3 at the same time for individuals with clinically mild or moderate sensitivity. Patches were kept in place for 4 hours. Patients were asked to return for reading 7 days after application of each test, and to call or take photographs of any significant reactions in shorter intervals of time. Tests were graded according to the scale of Marks for reaction grades 1-7, modified by the addition of grade 8 for distant reactions as described in the section on results (Table 1). Patients were tested with increasing concentrations of urushiol until at least one of duplicate patch tests produced a reaction equal to or greater than grade 3.

Patients electing immunotherapy received deltoid muscle IM injections of urushiol in 95% ethanol, beginning with 10 times the interpolated dose giving a grade 3 reaction, increasing by a factor of 3.16 every 1-2 weeks. The "Interpolation Factor" listed in Table 1 depicted at FIG. 1, is the multiplier of the dose producing reactions of grade 2-8 that the inventor estimated to be the dose that would yield a reaction of grade 3. Toxicity monitoring consisting of CBC with automated differential, UA with automated microscopic examination and comprehensive automated serum multichemistry profile were performed before treatment and after cumulative doses of 50-160 µg and 780-840 µg.

The bottom line (reaction grade 8) and the right hand column (interpolation factor) are the inventor's additions to the quantitative patch test assay used by Marks et al (Prevention of poison ivy and poison oak allergic contact dermatitis by quaternium-18 bentonite, J Am Acad Dermatol 1995 August; 33(2 Pt 1):212-6) to document the protective effect of a barrier product that was subsequently marketed as "Ivy Block." The reason for choosing this scale rather than the generally accepted standard scale for clinical use (which is qualitative rather than quantitative) is that the FDA accepted a reduction in sensitivity on the Marks scale as evidence confirming the barrier efficacy of that product (meaning that they can make that claim in their advertising and on their label). The precedent set by the FDA in accepting this assay as objective documentation of reactivity to urushiol in its approval of that claim for that product would make it difficult for them not to accept the same assay as objective documentation of the efficacy of my vaccine.

The inventor added grade "8" because some of the highly sensitive patients developed distant reactions at sites of recent previous poison ivy reactions. An interpolation factor was added based on a reaction grade of 3 to let the inventor quantitate response to treatment. In 2009 the inventor worked with a 2008 concentrate with a urushiol concentration of 1.13 mg/ml (solution "F0"). In 2010 he worked with a 2009 crude extract (made by eluting fresh leaves with ethanol) of 1.92 mg/ml (solution "G0"). Table 2 of FIG. 1 reports patients treated during 2009. The quantitative patch test is performed with 10 µl of urushiol solution, beginning with F2 or G2 (100-fold dilutions of F0 and G0, respectively) in patients who were not highly allergic by history, and with F2 or G3 in highly allergic patients. Patient #4 (last data column of Table 2) gave a grade 5 reaction to 10 µl of F3 before treatment. Using the interpolation factor of 0.45, I estimated that 10×0.45=4.5 µl×0.00113 µg/µl (urushiol concentration of dilution F3)=0.00509 μg urushiol needed to produce a grade 3 reaction. After treatment with a cumulative dose of 163 μg she required an interpolated 0.017 μg to produce a grade 3 reaction and after treatment with a total of 841 mg she required an interpolated 0.113 μg to produce the same reaction, a reduction in sensitivity by a factor of 22.2.

Urushiol patch testing was repeated in 3 of 4 patients at a cumulative dose of either ~50 or ~160 μg and in all patients at the end of treatment with a cumulative total dose of 780 or 840 μg. Patients were asked to report any adverse health experiences during the course of the study. The measured (for grade 3 reactions or interpolated (for other grades) dose of urushiol needed to provoke a grade 3 reaction is listed as "μg Urushiol" at baseline, mid-treatment ("Cum dose-1") and end-treatment ("Cum dose-2") in Table 2.

Results:

The urushiol concentrate was a slightly supersaturated dark green liquid in which a fine precipitate settled out with standing, was easily re-dissolved or suspended on swirling, and once present did not appear to increase in quantity over time. The urushiol content of this material was 1.13 mg/ml.

Pre-Tx patch tests: Five patients were tested, of whom three were clinically highly sensitive, one was moderately sensitive, and the first test subject (the author) was mildly sensitive. One highly sensitive patient demonstrated a minimal (grade+/−) reaction to patch testing with 10 μl of F3 (0.0113 μg). The others did not react to this dose. Two of three highly sensitive patients developed multiple mild (1) or moderate (1) distant poison ivy lesions (each >3 cm dia) at sites of previous reactions, 48 hours after patch test application, responding to standard poison ivy treatment with topical (1) or oral (1) corticosteroids. Neither developed a local reaction at the patch test site though this could have been blocked by treatment in the patient treated with prednisone. We defined distant reactions as grade 8 on Marks's scale of 1-7.

Laboratory monitoring for toxicity: CBC with automated differential count, UA with automated microscopy and comprehensive serum multichemistry profile were performed pre-treatment, at a cumulative treatment dose of 50-160 μg and following treatment at a cumulative dose of 780-840 μg. No abnormalities were found.

Responses to Tx are listed in Table 2 depicted at FIG. 1. One of three patients tested at 50-160 μg cumulative dose showed a reduction in sensitivity from baseline (3-fold), 3 of 4 showed a 3-22-fold reduction at a cumulative treatment dose of 780-840 μg. No patient demonstrated reduced sensitivity at a cumulative Tx dose <1500× the patch test dose needed to elicit a grade 3 reaction. Every patient receiving >2400 times the grade 3 patch test dose demonstrated reduced patch test sensitivity. Loss of sensitivity to natural exposure correlated with a cumulative treatment dose >34,000 times the pre-treatment patch test dose needed to elicit a grade 3 reaction. One of the responders, a tree trimmer with regular occupational exposure, remained resistant to natural exposure with reduced patch test sensitivity 9 months after completing treatment but experienced a relapse of both clinical and patch test sensitivity at 14 months.

Discussion:

In our patch test technique (the method of Marks), 10 μl of urushiol of known concentration is applied to the volar forearm on a 7 mm filter paper disc for 4 hours in a Finn chamber. This differs from the "classic" method of poison ivy patch testing in which a measured volume of urushiol in acetone is allowed to evaporate to dryness in an 8 mm diameter ring on the volar forearm. The Marks method has a track record of acceptance by regulatory authorities, a decrease in reactivity having been accepted by the US FDA as evidence of efficacy of the barrier product studied by Marks in the cited reference.

In references already cited previously, allergic Guinea pigs were desensitized to natural or synthetic urushiols in edible plant oils at cumulative doses of 16-20 mg per animal. Previously unexposed, non-allergic humans were tolerized by IM injections of urushiol in corn oil at cumulative doses of 16 mg. The inventor observed reduced patch test reactivity in 3 of 4 patients and a complete clinical remission in two at cumulative urushiol doses less than 1 mg.

The inventor proposes that IM injection in ethanol may be a more effective route of delivery than IM injection in edible plant oils because as the ethanol is diluted by interstitial fluids the urushiol precipitates in situ, leaving a reservoir of microscopic particles of precipitated allergen with a relatively large surface area for the mass of urushiol injected, in highly vascular muscle tissue. It is believed that the large surface area of urushiol in persistent intimate contact with interstitial fluid and the cells that traffic in that environment is somehow more effective at inducing cellular immune tolerance than any formulation for which outcomes have been reported.

88% of the urushiol was lost in the original 2008 extract in the concentration process because of failure to recognize the importance of controlling water content. The unconcentrated crude 2009 extract already contains 50% more urushiol per ml than the 2008 concentrate used in the present study. With better attention to water control the inventors believe they can make a 10-100 fold stronger vaccine for future use, possibly removing cholesterol (the major impurity) at the same time. In the present study the inventor chose to limit the individual IM deltoid muscle treatment dose to no more than 0.15 ml of <95% ethanol every 1-2 weeks, this not being appreciably > the 0.1 ml treatment dose to which the inventor had experienced no adverse effects in the 1980's. Applying the same dose volume limit to a 10-100 fold stronger vaccine should let us explore treatment with higher doses with hopefully equal safety but greater efficacy for patients like patient #1 in FIG. 1, Table 2, who was allergic, but not as highly sensitive as patients #2 and #4 who experienced complete clinical remissions.

This example considered methods and apparatuses for the efficient delivery of drugs. There are drugs for which the desired action is facilitated by the persistent presence of a relatively large surface area of the drug in contact with interstitial fluid in a richly vascularized tissue such as muscle.

The necessary physical properties for a drug to be deliverable by this means were considered to be the following:

1. Solubility in a non-aqueous solvent that is readily miscible with water, and of which small volumes can be safely injected into muscle.
2. Insolubility in aqueous media, most specifically insolubility in interstitial fluid.

The effectiveness of this drug delivery system was discovered in connection with the finding that an investigational poison ivy vaccine administered by intramuscular injection in ethanol was effective at much lower doses than similar vaccines injected in corn oil in previously published studies.

The inventors' interpretation is that as the small volume of injected ethanol is rapidly diluted by interstitial or tissue fluid following injection into muscle, large numbers of very small particles of the alcohol-soluble, water-insoluble drug precipitate in place. The inventors' interpretation is that as the small volume of injected ethanol is rapidly diluted by interstitial fluid following injection into muscle, large numbers of very small particles of the alcohol-soluble, water-insoluble drug precipitate in place. They either persist in place because of their water-insolubility and they expose a relatively large surface area to interstitial or tissue fluid and to cells that traffic in interstitial fluids because of their small size, or alternatively they may be taken up and processed by certain of these trafficing cells.

The traditional vehicles for the injection of lipid-soluble, water-insoluble drugs are vegetable oils such as corn oil. The bolus of drug injected in corn oil remains in it lipid vehicle and presents a much smaller surface contact area to interstitial fluid and to the cells and biologically active chemicals that traffic through it than is achieved by intramuscular injection in alcohol.

It is possible that the actual mechanism of drug delivery is different from this interpretation, which will not be known without studies for which there has been no reason prior to our recent discovery of the increased efficacy of this method. The inventors believe that they are the first to document that the use of alcohol as a vehicle results in greater therapeutic effect.

Ethyl alcohol (ethanol) at concentrations up to 95% is believed to be a good vehicle for the present compositions and methods, as it appears to be non-toxic when injected into muscle in small volumes, there are many drugs that are highly soluble in ethanol at concentrations up to 95%, that are insoluble in water or interstitial fluid, and whose mechanism of action is facilitated by the persistent exposure of large surface areas of drug to migrating cells and interstitial or tissue fluids. Ethanol may be used at concentrations up to 100% if pharmaceutical grade absolute ethanol is used.

Ethanol-soluble, water-insoluble allergy vaccines are good drugs for use with this delivery system as their beneficial action is facilitated by the persistent contact of large surface areas of drug with the aqueous phase extracellular fluid milieu of a richly vascularized tissue such as muscle. However, the present drug delivery system and mechanism, including the present compositions and methods, are not limited to ethanol as a solvent and to water-insoluble allergy vaccines as drugs.

Example 2

This prophetic example considers methods of providing immuno-therapy for peanut allergens in particular.

The challenge in allergen immunotherapy is to deliver a sufficient quantity of an appropriately configured allergen to cellular microenvironments associated with the development of immunologic tolerance (tolerogenicity), without enough reaching effector signaling microenvironments to trigger allergic reactions (allergenicity). The inventor discovered that in chronic severe poison ivy, immunotherapy with a vaccine formulated to precipitate large numbers of small particles with a large surface area in intimate contact with the cells and cytokines that circulate through muscle, was ~200 times more effective at tolerogenicity than the same allergen given by the traditional route, subcutaneous injection in corn oil. Because the process by which tolerogenesis must occur is the same for both peanut allergy and poison ivy (1), the inventor wants to make and study the immune response of appropriately formulated peanut allergy vaccines using the same delivery system A way to formulate a vaccine of Ara h2 (the major peanut allergen) with the necessary solubility properties is to polymerize Ara h2 molecules into allergoids, which constitute a separate and time honored method of favoring the balance between tolerogenicity and allergenicity (2). Allergoids given by the traditional route of subcutaneous (human) or intraperitoneal (animal) injection in Alum have not been shown to by themselves to induce tolerance in peanut allergy.

The inventor plans to produce Ara h2 allergoids with the solubility properties needed to synergistically exploit the enhanced tolerogenesis achieved by precipitation of small particles in muscle, and compare their immune system uptake and response to those of the same allergoids administered by traditional means in a mouse model that could subsequently be used to study response to immunotherapy.

Significance/Relevance of the Concept:

Anaphylactic IgE-mediated peanut allergy is an increasingly common cause of morbidity, mortality and utilization of health care economic resources with a major but poorly understood genetic component (3) and no safe, simple and effective treatment. The inventors' synergistic application of two methods to enhance T-cell tolerogenesis offers the potential to achieve such a treatment.

Hypothesis/Concept:

The poison ivy allergen, urushiol, is soluble in 95% ethanol but insoluble in water. Intramuscular injection of urushiol in small volumes of 95% ethanol results in precipitation of large numbers of small insoluble particles as the ethanol is rapidly diluted by interstitial or tissue fluid, resulting in a ~200-fold enhancement of tolerogenesis per mg administered urushiol. As the most practical way to make an Ara h2 vaccine with the solubility properties needed to exploit the benefit of this delivery system may be a derivative of a process already known to enhance tolerogenesis, we have the opportunity to see if the synergistic application of two methods of tolerogenesis enhancement yields a sufficiently high ratio of tolerogenicity to allergenicity to constitute a predictably safe and effective treatment for peanut allergy.

Objectives:

1) Synthesize allergoids of Ara h2 that are insoluble in water but highly soluble in 95% ethanol or other water-miscible solvents of which small volumes can be safely injected into muscle. 2) Identify particle size and stability following injection into muscle in a mouse model. 3) Determine whether injected allergoid remains in situ or is taken up by dendritic cells, as this would define parameters to be measured in subsequent studies of immunotherapy efficacy.

Methods:

Synthesis: Standard cross-linking of Ara h2 with glutaraldehyde &/or formaldehyde. Evaluation of products of differing molecular size and cross-link density for appropriate solubility. Addition of hydrophilic or hydrophobic sidechains by standard methods of protein chemistry as needed to optimize solubility profile.

Analysis:

Comparison of mouse immune response to fluorescein labeled and unlabeled allergoid administered by traditional (intraperitoneal in alum) and experimental (intramuscular in ethanol or alternate solvent) routes. Compare uptake by circulating antigen-presenting cells by fluorescence-activated cell sorting and study persistence of allergen in situ and migration into regional lymphoid tissue.

The strategies of interest involve one or more of modifying an allergen, modifying the way it is delivered, and modifying the response of various host receptor and antigen processing tissues. The common goal is to increase the efficiency with which allergen is delivered to the cells and microenvironments associated with the induction of tolerance and reduce its exposure to the cells and microenvironments that favor the triggering of allergic reactions. The present inventor proposes to combine two different methods of this type. One, the polymerization of allergen molecules by cross-linking to form allergoids, has been known for decades but never found by itself to provide sufficient control of allergen trafficing for safe peanut allergy immunotherapy. The other, formulation of a vaccine with solubility properties that precipitate large numbers of small particles of allergen with a large total surface area in intimate contact with the cells and cytokines that circulate through muscle tissue, is novel and has not previously been applied to diseases of humoral immunity. The inventor believes that a synergistic combination of the two methods has the potential to achieve sufficient control of allergen trafficing to permit safe, effective and reliable immunotherapy for peanut allergy.

The scope of work to be performed with this includes the production of allergoids of major peanut allergen Ara h2 that are insoluble in water and interstial or tissue fluid but highly soluble in either 95% ethanol or in another solvent that mixes freely with water and of which small volumes can safely be injected into muscle. The inventor will then inject these vaccines to the thigh muscle of mice and track their clearance by quantitative immune analysis of the serum and the local muscle tissue. It is hypothesized that precipitation into large numbers of small particles occurs as the ethanol or other solvent is rapidly diluted by interstitial or tissue fluid following injection. Fluorescein labeling of the allergoid and Fluorescence Activated Cell Sorting (FACS) analysis will be used to assess uptake by antigen presenting cells and to follow the persistence of allergen in situ, and of the labeled antigen processing cells migration into regional lymphoid tissue. These studies may shed light on which of two possible mechanisms of tolerogenesis predominates: long term persistence in situ until the injected allergen is tolerated like self, or uptake by dendritic cells with further processing in regional lymph nodes. Allergenicity of the Ara h2 and the allergoid preparations delivered into either conventional sites (intraperitoneally) or intramuscularly, will be compared by assessing the cytokine and immunoglobulin profile of the mice.

It is believed that successful completion of this project will lead to both trials of immunotherapy in a mouse model of peanut allergy and further mechanistic studies to investigate the immune processes that operate during induction of tolerance to allergen exposure Although the present disclosure has been described in example embodiments, additional modifications and variations would be apparent to those skilled in the art. It is therefore to be understood that the present disclosure herein may be practiced other than as specifically described. Thus, the present embodiments should be considered in all respects as illustrative and not restrictive. Accordingly, it is intended that such changes and modifications fall within the scope of the present disclosure as defined by the claims appended hereto.

What is claimed is:

1. A method of treating allergies comprising
   administering to a subject having an allergy to poison ivy, poison oak and/or poison sumac an allergen immunotherapy formulation comprising:
   a pharmaceutically acceptable extracted and concentrated urushiol; and
   a pharmaceutically acceptable non-aqueous solvent,
   wherein the non-aqueous solvent is miscible with water and interstitial fluid; and
   wherein the extracted and concentrated urushiol is selected to be, synthesized to be, or modified to be insoluble in water and in interstitial fluid, and soluble in the solvent;
   such that the urushiol is capable of being deposited atraumatically in microscopic particles in tissue of the subject surrounding an administration site as the formulation is diluted by fluids present in the tissue into which it is administered and the urushiol becomes insoluble, wherein said administering comprises injecting the formulation into muscle of the subject.

2. The method of claim 1, wherein the subject is a mammal.

3. The method of claim 1, wherein said non-aqueous solvent comprises at least one solvent selected from the group consisting of ethanol, ethyl acetate, acetonitrile, and dimethylsulfoxide.

* * * * *